United States Patent [19]

Demarne et al.

[11] Patent Number: 4,510,315
[45] Date of Patent: Apr. 9, 1985

[54] 4[3-(1,1-DIMETHYL-2-3(3-INDOLYL)E-THYLAMINO)-2-HYDROXYPROPOXY]INDOLE

[75] Inventors: Henri Demarne; Jean Wagnon, both of Montpellier, France

[73] Assignee: Sanofi, S.A., Paris, France

[21] Appl. No.: 530,699

[22] Filed: Sep. 9, 1983

Related U.S. Application Data

[62] Division of Ser. No. 178,550, Aug. 15, 1980, Pat. No. 4,404,217.

[30] Foreign Application Priority Data

Sep. 17, 1979 [FR] France ................................ 70 20907

[51] Int. Cl.$^3$ ............................................ C07D 403/12
[52] U.S. Cl. ............................................................ 548/455
[58] Field of Search .......................................... 548/455

[56] References Cited

U.S. PATENT DOCUMENTS 3,947,584  3/1976  Zirngibl et al. ................ 424/274
4,234,595  11/1980  Kreighbaum et al. .......... 424/274

FOREIGN PATENT DOCUMENTS 2001633  2/1979  United Kingdom .

OTHER PUBLICATIONS

Jackman, et al., J. Pharm. Pharmacol., 17:742–746 (1965).

Primary Examiner—Glennon H. Hollrah
Assistant Examiner—D. B. Springer
Attorney, Agent, or Firm—Arnold, White & Durkee

[57] ABSTRACT

The present invention discloses a 4-[3-(1,1-dimethyl-2-3(3-indolyl)ethylamino)-2-hydroxypropoxy]indole of formula

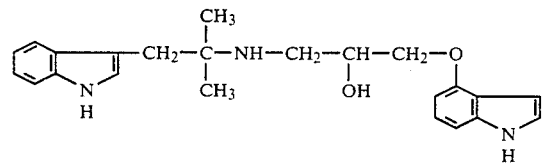

and pharmaceutically acceptable acid salts thereof, which are particularly active on the cardiovascular system.

2 Claims, No Drawings

4[3-(1,1-DIMETHYL-2-3(3-INDOLYL)E-THYLAMINO)-2-HYDROXYPROPOXY]INDOLE

This is a division of application, Ser. No. 178,550, filed Aug. 15, 1980, now issued as U.S. Pat. No. 4,404,217 on Sept. 13, 1983.

The present invention relates, by way of novel products, to chemical substances derived from indole as well as their acid addition salts and the isomers of said derivatives.

The invention also relates to a process for the preparation thereof and application thereof in therapeutics.

The compounds according to the invention are chosen from the group constituted by:

(a) the compounds having the general formula:

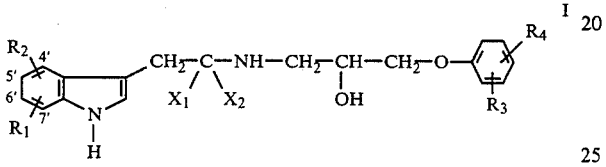

in which:

$R_1$ and $R_2$ each designate, independently, an atom of hydrogen or an atom of halogen, a lower alkyl group, a lower alkoxy group, occupying one of the positions 4' to 7' of the indole ring;

$R_3$ and $R_4$ considered independently, designate an atom of hydrogen, a lower alkyl, a lower alkoxy, an atom of halogen, a nitro group, an acyl $R_5CO$ group, an alkylthio $R_5S$ group or alkylsulfinyl $R_5SO$ or alkylsulfonyl $R_5SO_2$ in which $R_5$ designates a lower alkyl or cycloalkyl group;

$R_3$ and $R_4$ may also designate $(CH_2)_n COOR_6$ group or $(CH_2)_n CONH-R_6$ or $(CH_2)_n NHCOOR_6$ or $(CH_2)_n NHCOR_6$ group in which n represents an integer from 0 to 2 and $R_6$ designates a lower alkyl group;

finally, $R_3$ and $R_4$ taken together may form a cycle possibly comprising the heteroatom so as to constitute, with the benzene ring a nucleus to which they are bonded, a bicyclic ring structure, and in particular:

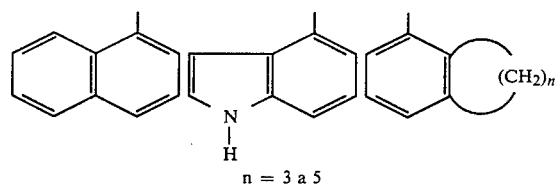

n = 3 a 5

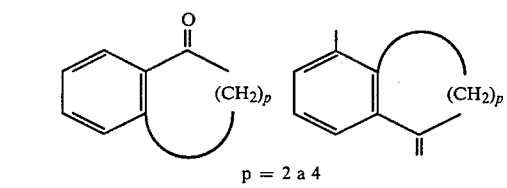

p = 2 a 4

$X_1$ represents an atom of hydrogen, a lower alkyl group, a hydroxymethyl group or a $COOR_7$ group in which $R_7$ represents hydrogen or a lower alkyl group;

$X_2$ represents hydrogen or, in the case of

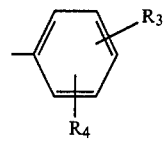

representing a bicyclic ring other than naphthyl, $X_2$ may be a methyl group.

(b) The addition salts which compounds I are capable of giving with the pharmaceutically acceptable inorganic or organic acids such as hydrochloric acid, citric acid, maleic acid, fumaric acid, tartric acid.

In the present specification, lower alkyl group is understood to mean a linear or branched alkyl group comprising from 1 to 5 atoms of carbon.

Compounds I, when

is not an asymmetric carbon, comprise only one asymmetric carbon atom at the alcohol function and may therefore exist in the form of two optical isomers R and S. When

is itself an asymmetric carbon atom, the compounds 1 possess two centres of asymmetry and consequently there are 4 stereoisomers: RR, RS, SR and SS. Both the optical isomers and the stereoisomers are an integral part of the invention.

Compounds I may be obtained according to the following reaction diagram:

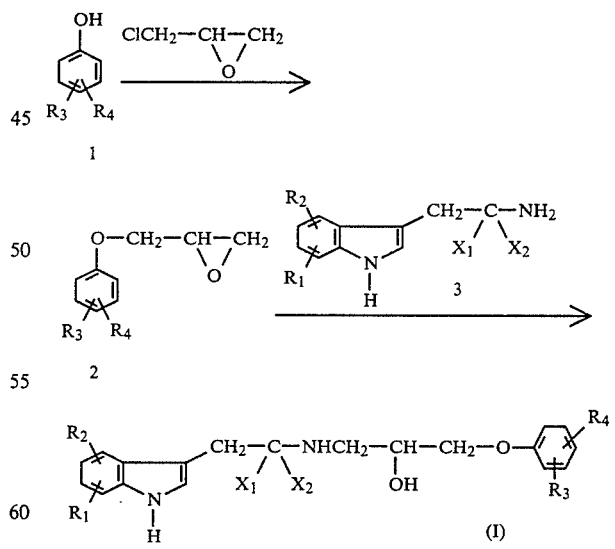

By the action of epichlorohydrine on a suitably substituted phenol 1, within an anhydrous solvent such as ethanol at reflux and in the presence of an alkaline agent, the epoxide 2 is obtained which is opened by action of a suitably chosen amine 3 within an anhydrous solvent such as ethanol.

When

is not an asymmetric carbon, the products I are obtained in the form of a mixture of the optical isomers R and S which may be separated by the conventional methods of resolution, in particular by combination within a suitable solvent with an optically active acid such as tartric D and L or benzoyl tartric D and L acids.

When

is an asymmetric carbon atom, the reaction leads to 4 stereoisomers. By using an amine 3 previously separated into its isomers $R_1$ and $S_1$, it is possible to obtain, directly from the racemic of 2 ($RS_2$), each of the two isomers $(RS)_2$—$R_1$ and $(RS)_2$—$S_1$. Each of these isomers may then be resolved by the conventional methods of fractionated crystallisations and leads to the four isomers: $R_2 R_1$, $S_2 R_1$, $R_2 S_1$, $S_2 S_1$.

The compounds in which $X_1$=$CH_3$, $X_2$=H may also be obtained from an acetonyl indole and from a phenoxy-1 amino-3 propanol-2:

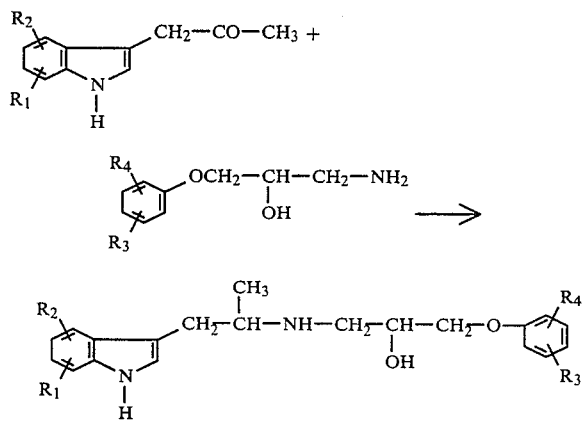

Condensation takes place by mixture of the reagents within a solvent such as a lower aliphatic alcohol at low temperature and preferably at ambient temperature. The intermediate imine formed is reduced without isolation by a reducing agent such as sodium borohydride.

In the case of derivatives of tryptophanol ($X_1$=$CH_2OH$, $X_2$=H), it is possible to effect a stereoselective synthesis of the four isomers of compounds I. In fact, it is known that the reduction of an optical isomer or tryptophane leads to the optically active tryptophanol.

Thus, L-tryptophane leads to S-tryptophanol and, inversely, D-trytophane yields R-tryptophanol. (Biochimica Biophysica Acta 341, 284, 1974).

By condensation of one of the optical isomers with a racemic epoxide 2, a mixture of compounds $S_1R_2+S_1S_2$ is obtained from S-tryptophanol and $R_1R_2+R_1S_2$ is obtained from R-tryptophanol.

Each of the isomers in the pure state may be separated from these mixtures by crystallisations.

Finally, in the particular case of the derivatives of tryptophanol where $R_4$=$CH_3$ in the ortho position and $R_5$=H, it is possible to synthesize the four isomers of (I) directly.

In fact, it is known (J. Chem. Soc. Chem. Comm. 1973, 896) that the diol:

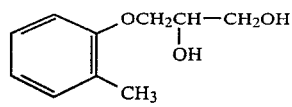

may be separated into its isomers R and S.

Each of the isomers, tosylated on the primary alcohol function, is condensed with each of the isomers of the tryptophanol by heating within an inert solvent such as acetonitrile. The four isomers of the corresponding compound I are thus obtained.

The following examples illustrate the invention without limiting the scope thereof.

EXAMPLE 1

N-[(chloro-2 propionyl-4 phenoxy)-3 hydroxy-2 propyl](amino-2 propyl)-3 indole, acid fumarate (CM 7743)

(I) $R_1$=$R_2$=H; $X_1$=$CH_3$; $X_2$=H; $R_3$=2—Cl; $R_4$=4—$COCH_2CH_3$ 1-(Chloro-2 propionyl-4 phenoxy)-1 epoxy-2,3 propane 2.5 g of chloro-2 propionyl-4 phenol and 10 ml of epichlorohydrine are dissolved in 20 ml of absolute ethanol. 0.9 g of sodium hydroxide are added and the mixture is taken to reflux for 2 hours.

50 ml of water is added to the mixture which is then extracted with methylene chloride. The organic phase is washed with water, dried over sodium sulfate and evaporated to dryness.

3 g of the expected product are obtained, used as such for the following operation.

2-CM 7743

The epoxide obtained hereinabove (3 g) and 2 g of (amino-2 propyl)-3 indole are dissolved in 50 ml of absolute ethanol. The mixture is heated to reflux for 6 hours then the solvent is evaporated. The crude product thus obtained, dissolved in ethyl acetate is passed over a column of silica. By eluting by a mixture of methanol-ethyl acetate (10–90 vol/vol), the pure base is obtained (2.85 g).

This base dissolved in an ethanol-acetone mixture is treated hot by an equimolecular quantity of fumaric acid. By cooling, the neutral fumarate crystallises: m.p. 118°–122° C.

EXAMPLE 2

N-[(methyl-2 phenoxy)-3 hydroxy-2propyl]DL tryptophane CM7897

(I) $R_1$=$R_2$=H; $X_1$=COOH; $X_2$=H; $R_3$=2—$CH_3$; $R_4$=H 8.7 g of DL tryptophane and 1.7 g of sodium hydroxide are dissolved by heating in 30 ml of dimethylformamide. 7 g of (methyl-2 phenoxy)-1 epoxy-2.3 propane are added to the solution which is boiled for 3 hours.

The solvent is evaporated in vacuo. The residue is taken up with 200 ml of water and the pH is adjusted to 7. A precipitate is formed which is drained and washed twice with boiling methanol. Colourless crystals are obtained (4.5 g); m.p. 220°–1° C.

By operating according to the process of examples 1 or 2, but varying the substituents $R_1$, $R_2$, X, $R_3$, $R_4$ and $R_5$, the products shown in Table I hereinafter are obtained.

Similarly, by replacing the starting monocyclic epoxide by an epoxide resulting from a bicyclic phenol, the compounds (I) shown in Table II hereinafter are obtained.

EXAMPLE 3

N-(phenoxy-3 hydroxy-2 propyl)(amino-2 propyl)-3 indole (CM 7783)

(I) $R_1=R_2=H$; $X_1$ $CH_3$; $X_2=H$; $R_3=R_4=H$

The mixture of 2.9 g of phenoxy-3 hydroxy-2 propylamine and 3 g of acetonyl-3 indole in 75 ml of absolute ethanol is heated under reflux for one night.

The solution is cooled in an ice bath and a suspension of 4 g of sodium borohydride in 10 ml of a water-ethanol (50—50 vol/vol) mixture is slowly added. The mixture is left with stirring for two and a half hours at ambient temperature then the excess of borohydride is destroyed by addition of dilute acetic acid.

The mixture is evaporated to dryness and the residue is taken up with dilute sodium hydroxide. It is extracted three times with ethyl acetate, the solution is washed with water and dried over sodium sulfate. It is chromatographed on a column of silica gel. By eluting with a (7—3 vol/vol) mixture of ethyl acetate-methanol, a product which crystallises is obtained Weight 2.75 g.

After two recrystallisations in the mixture of methylene chloride-isopropylic ether; m.p.: 124°–6° C.

EXAMPLE 4

RS(−)N-[(methyl-2 phenoxy)-3 hydroxy-2 propyl]tryptophanol (CM7903)

(I) $R_1=R_2=N$; $X_1=CH_2OH$; $X_2=H$; $R_4=2-CH_3$; $R_5=H$

1-S(+)(methyl-2 phenoxyl)-1 toxyloxy-3 propanol-2

5.5 g of R (methyl-2 phenoxy)-1 propane diol-2.3 are dissolved in 25 ml of dry pyridine, and the solution is cooled to −13° C. 5.75 g of freshly recrystallised para-toluene sulfonyl chloride are then added in 30 minutes in small fractions. The mixture is left for 8 days at 0° C. Ethyl acetate (100 ml) is then added, then a 20% solution of sulfuric acid (150 ml), with stirring and cold. The organic phase is separated then the aqueous phase is reextracted three times with ethyl acetate. The organic extracts are joined, washed with water up to neutrality and dried over sodium sulfate. They are evaporated to dryness at 50° C. in vacuo.

The residual oil is chromatographed on a column of silica gel. The tosylate is eluted by pure ether and an oily product is obtained (7.85 g)$\alpha_D^{26}=+12.8$ (C=8.39; chloroform).

2-CM 7903

The mixture of 3.8 g of the preceding tosylate and 4.3 g of S(−)tryptophanol in 70 ml of acetonitrile is heated to reflux for 26 hours.

The mixture is evaporated to dryness then the residue is taken up in ethyl acetate. This solution is stirred for 2 hours at ordinary temperature with a diluted solution of sodium hydroxide. The organic phase is separated and the aqueous phase is reextracted three times with ethyl acetate. The organic extracts are joined, washed with water and dried over sodium sulfate.

The oil thus obtained is chromatographed on a column of silica gel. With a (90—10 vol/vol) mixture of ethyl acetate-methanol an oily, still impure product is eluted.

It is purified by formation of fumarate in the ethanol-ethyl acetate mixture. The crystallised fumarate is decomposed by sodium hydroxide and yields a crystallised base. Recrystallisation is effected twice in a mixture of dichloromethane-isopropyl ether and a solid is finally obtained (1.2 g); m.p. 107°–9° C.; $\alpha_{589}^{25.5}=-17$; $\alpha_{500}^{25.5}=-30$; $\alpha_{350}^{25.5}=-97$; (C=0.6; methanol)

EXAMPLE 5

SS(−)N-[(methyl-2 phenoxy)-3 hydroxy-2 propyl]tryptophanol (CM7898)

1-R(−)(methyl-2 phenoxy)-1 toxyloxy-3 propanol-2

Operation is the same as in Example 4.1—replacing the R (methyl-2 phenoxy)-1 propane diol-2.3 by the isomer S.

In the same way, the expected product is obtained in the form of oil; $\alpha_D^{26}=12.4$ (C=8.0; chloroform).

2-CM 7898

Operation is carried out as in Example 4.2-, replacing the isomer S(+) of tosylate by the isomer R(−) obtained hereinabove.

In the same way, CM 7898 is obtained.

m.p. 150°–1° C.; $\alpha_{589}^{25.5}=-12.8$; $\alpha_{500}^{25.5}=-19.5$; $\alpha_{350}^{25.5}=-54.5$ (C=0.6; methanol).

EXAMPLE 6

By operating as in Examples 4 and 5 but by replacing the S(−) tryptophanol by R(+) tryptophanol, the following is obtained, in the same way: -RR(+)N-[(methyl-2 phenoxy)-3 hydroxy-2 propyl]tryptophanol (CM 7902); m.p.: 150.5°–151.5° C.

$\alpha_{589}^{25.5}=+14$; $\alpha_{500}^{25.5}=+19$; $\alpha_{350}^{25.5}=54$ (C=0.6; methanol);

- and SR(+)N-[methyl-2 phenoxy)-3 hydroxy-2 propyl]tryptophanol (CM 7899); m.p. 107°–8° C.

$\alpha_{589}^{25.5}=+18.2$; $\alpha_{500}^{25.5}=+28$; $\alpha_{350}^{25.5}=+96$ (C=0.6; methanol).

EXAMPLE 7 RS(+) and SS(−)N-[(methyl-2 phenoxy)-3 hydroxy-2 propyl]tryptophanol (CM 7903 and 7898)

3.35 g of S(−)tryptophanol and 2.9 g of racemic (methyl-2 phenoxy)-1 epoxy-2.3 propane in 70 ml of ethanol are heated to reflux for 2 hours. By concentration of the solvent in vacuo, a crystallised solid is obtained which is drained and recrystallised three times in a methanol-ethyl acetate mixture.

Finally, 0.65 g of crystals are obtained. m.p. 150°–151.5° C.

$\alpha_{589}^{25.5}=-13.5$; $\alpha_{500}^{25.5}=-21.5$; $\alpha_{350}^{25.5}=-56$; (C=0.6; methanol)

This product is identical to that of Example 5; CM 7898.

The mother liquors of the crystallisation and of the first recrystallisation are joined and chromatographed on silica gel as indicated in Example 4.

The solid obtained is purified by formation then decomposition of the fumarate (cf. Example 4) and finally yields 0.69 g of crystals after 2 recrystallisations in the mixture of dichloromethane-isopropyl ether; m.p.: 106°–7° C.

$\alpha_{589}^{25.5} = -17$;  $\alpha_{500}^{25.5} = -27$;  $\alpha_{350}^{25.5} = -96.5$; (C=0.62; methanol)

This product is identical to the one obtained in Example 4; CM 7903.

The products of the invention have been studied with a view to determining their pharmacological activity and more especially their activity on the cardiovascular system.

The products of the invention have been submitted to the pharmacodynamic tests indicated hereinbelow.

In vivo pharmacological action in the dog

The dog is anaesthetized using sodium pentobarbital, administered by the IV route at a dose of 30 mg/kg. A cannula placed in the saphenous vein allows the intravenous injections of the products. The animal is submitted to intubation and is allowed to breathe spontaneously.

The cardiac frequency and the systemic arterial pressure are studied and the variations of these parameters are observed after intra-venous injection of the product to be tested. Each product is tested with increasing doses.

Antagonism of the effects of isoprenaline

The antagonism of the products with respect to the β stimulant cardio-vascular effects of isoprenaline on the β adrenergic receptors has been sought. The results are presented in Table III and expressed in ID$_{50}$: the dose expressed in mg/kg which provokes the inhibition by 50% of the tachycardia ($\beta_1$) and hypotension ($\beta_2$) induced by the isoprenaline administered by the IV route. The last column indicates the cardioselectivity ($\beta_1 > \beta_2$) or a low cardioselectivity $\beta_1 > \beta_2$, or no cardioselectivity $\beta_1 < \beta_2$ and $\beta_1 = \beta_2$.

Antagonism of the effects of noradrenaline

The antagonism of the products with respect to the vascular effects provoked by the IV administration of noradrenaline on the α adrenergic receptors has been sought. The results presented in Table III are expressed in ID$_{50}$: it is the dose (mg/kg) which provokes the inhibition by 50% of the pressure response due to the IV administration of noradrenaline.

Pharmacological action in vitro

"Binding" tests

The binding tests are effected on suspensions of plasmic membranes coming from various organs. The suspensions of membranes are placed in incubation with the tritiated ligand and various concentrations of products to be tested. After incubation, each test is filtered on GFB(Whatman) filter, the filters are dried and introduced into counting flasks. The measurement of the radioactivity is assessed by scintillation in a liquid medium. The results are expressed in EC$_{50}$ of displacement of the tritiated ligand, i.e. the concentration of the product which displaces 50% of the radioactivity of the ligand.

Power of displacement of the $^3$H dihydroalprenolol

The tests were made on plasmic membranes of hearts of dogs ($\beta_1$ receptor) and lungs of rats ($\beta_2$ receptors), in the presence of $^3$H dihydroalprenolol $4 \times 10^{-9}$ M.

Power of displacement of the $^3$H clonidine, and of the $^3$H WB 4101

The tests were made on plasmic membranes of rat brains, in the presence of $^3$H clonidine $1.2 \times 10^{-9}$ M ($\alpha_2$ receptor) and of $^3$H WB4101 (N-[2-(2.6 dimethoxyphenoxy)ethyl]1.4 benzodioxane-2-methylamine), $0.2 \times 10^{-9}$ M ($\alpha_1$ receptor).

The results concerning various products according to the invention are shown in Table III. At the end of the Table are shown, by way of controls, on the one hand the propanolol whose beta adrenergic blocking activity is well known and on the other hand a product whose structure is fairly close to that of the products of the invention included in the general formula of Belgian Patent No. 868 943. CM 7854 designates N-[(methyl-2 phenoxy)-3 hydroxy-2 propyl](amino-2 methyl-2 propyl)-3 indole.

These results show that the compounds according to the invention present a considerable inhibiting activity on the beta adrenergic receptors, which activity is often superior to that of propanolol.

Certain of these products are cardioselective in vivo (selectively inhibit the cardiac receptors: $\beta_1$, test with isoprenaline); these are CM: 7744, 7748, 7782, 7798, 7808, 7859, 7983 and 40038. This in vivo cardioselective note has been confirmed in vitro for certain products such as CM 7748 and 7798 which have a clearly greater affinity for the $\beta_1$ receptors (heart) than for the $\beta_2$ receptors (lungs).

All these products as beta adrenergic blocking agents have a duration of action which varies from 2 hours to more than 4½ hrs, when they are administered by the IV route.

Certain products have, in addition to their betalytic power, an alphalytic note. In vivo (test of noradrenaline), these are, in particular, CM 7743, 7764, 7748, 7782, 7806, 7808, 7824, 7859, 7903 and 40038. In vitro, these products have no affinity for the receptor with clonidine ($\alpha_2$). On the contrary, the products CM 7744, 7806, 7808, 7824, 7874 and 7983 have an affinity for the receptor with WB 4101 ($\alpha_1$).

The CM 7748, 7782, 7798, 7859 and 7874 provoke a bradycardia (from 10 to 20%) in the anaesthetised animal.

The CM 7744, 7806, 7808, 7824, 7874, 7898, 7899, 7902, 7903, 7906 and 40038 provoke a reduction in the peripheral arterial pressure when they are administered by the IV route in the anaesthetised dog.

The anti-aggregating activity of the CM 7743, 7744, 7824, 7854, 7859 and 7874 has been studied according to the BORN technique on plasma rich in platelets of human origin. ADP has been used as indicator of platelet aggregation. All the products tested have inhibited the platelet response with respect to the ADP. The required concentration for inhibiting by 50% the maximum rate of aggregation varies from 45 to 100 μM.

According to the pharmacological results obtained, the products according to the invention may be used for the following therapeutical indications Treatment of pathological disorders in connection with a hyperproduction of catecholamine: tachycardia, palpitations, extrasystoles and hypertension.

Basic treatment of hypertension.

Basic treatment of anginous complaint, the sequelae of infarctus, disorders in the auricular and ventricular rhythm.

These products may be presented in the different forms adapted for oral administration such as tablets dosed at 10 to 100 mg or for rectal administration such as suppositories dosed at 10 to 100 mg or in the form of injectable preparations containing from 5 to 50 mg of active ingredient.

The usual dosage is from 2 to 4 20 mg tablets per day, but exceptionally, under medical supervision, it may exceed these figures.

A few examples of galenical preparations are given hereinafter:

Tablets:

| | |
|---|---|
| CM 7748 | 20 mg |
| Microcrystalline cellulose | 160 mg |
| Lactose | 172 mg |
| Magnesium stearate | 8 mg |
| | 360 mg |

Suppositories

| | |
|---|---|
| CM 7898 | 40 mg |
| Suppocire C (injectable mixture of esters of natural fatty acids) Labrafil 2130 C (interesterified hydrogenated palm oil) | qsp 3 grams |

TABLE I

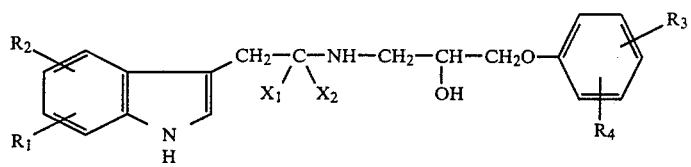

| code No. | $X_1$ | $X_2$ | $R_1$ | $R_2$ | $R_3$ | $R_4$ | Salt or base | Melting point (°C.) (solvant of cristallisation) |
|---|---|---|---|---|---|---|---|---|
| 7761 | H | H | H | H | 3-CH$_3$ | H | Base | 120 (ethyl acetate) |
| 7783 | CH$_3$ | H | H | H | H | H | Base | 124–6 (dichloromethane-isopropyl ether) |
| 7785 | " | " | H | H | 4-F | H | Base | 123–4 (dichloromethane-isopropyl ether) |
| 7808 | " | " | H | H | 2-NO$_2$ | H | Base | 84–6 (dichloromethane-isopropyl ether) |
| 7806 | " | " | H | H | 2-Cl | H | Fumarate (neutral) | 119–122 (ethanol-ethyl acetate) |
| 7744 | " | " | H | H | 2-CH$_3$ | H | Hydrochloride | 131–5 (dichloromethane-ethyl acetate) |
| | | | | | | | Neutral fumarate | 195–9 (75% ethanol) |
| 7983 | " | " | 5'-F | H | 2-CH$_3$ | H | Fumarate (acid) | 140–3 (ethyl acetate-ether) |
| 7782 | " | " | H | H | 3-CH$_3$ | H | Fumarate neutral | 172–4 (ethyl acetate-ethanol) |
| 7784 | " | " | H | H | 4-CH$_3$ | H | Fumarate (acid) | 180–2 (ethyl acetate-ethanol) |
| 7824 | " | " | H | H | 2-C≡N | H | Hydrochloride | 95 (ether) |
| 7904 | CH$_3$ | H | H | H | 2-C$_6$H$_5$—C(=O)— | H | Fumarate (neutral) | 176–8 (ethyl acetate-ethanol) |
| 7894 | COOCH$_3$ | H | H | H | 4-F | H | Hydrochloride | 76–8 (ether) |
| 7897 | COOH | H | H | H | 2-CH$_3$ | H | Base | 220–1 (methanol) |
| 7803 | H | H | H | H | 4-CH$_3$CH$_2$CO— | H | Base | 130–1 (ethyl acetate-methanol) |
| 7861 | H | H | 5'-OCH$_3$ | H | 4-CH$_3$CH$_2$CO— | 2-Cl | Base | 113–4 (dichloromethane-isopropyl ether) |
| 7802 | CH$_3$ | H | H | H | 4-CH$_3$CH$_2$CO— | H | Base | 118–120 (dichloromethane-isopropyl ether) |
| 7743 | " | " | H | H | 4-CH$_3$CH$_2$CO— | 2-Cl | Fumarate (neutral) | 119–122 (acetone-methanol) |
| 7595 | " | " | H | H | 4-CH$_3$CH$_2$CO— | 3-Cl | Base | 100–103 (dichloromethane-isopropyl ether) |
| 7801 | " | " | 5'-Cl | H | 4-CH$_3$CH$_2$CO— | 2-Cl | Base | 147 (isopropyl ether-methanol) |
| 7820 | " | " | 5'-OCH$_3$ | 6'-OCH$_3$ | 4-CH$_3$CH$_2$CO— | 2-Cl | Base | 127–130 (isopropyl ether) |
| 7825 | CH$_3$ | H | H | H | 4-CH$_3$(CH$_2$)$_4$—CO— | 2-Cl | Fumarate (neutral) | 165–6 (ethanol-ether) |
| 7844 | " | " | H | H | 4-(cyclopropyl)-CO— | 2-Cl | Fumarate (neutral) | 120–4 (isopropyl ether-methanol) |
| 7845 | C$_2$H$_5$ | H | H | H | 4-CH$_3$CH$_2$CO— | 2-Cl | Fumarate (neutral) | 170–2 (ethanol) |
| 7809 | CH$_2$OH | H | H | H | 4-CH$_3$CH$_2$CO— | 2-Cl | Base | 147–9 (ethanol) |
| 7988 | CH$_3$ | H | H | H | 4-CH$_3$CH$_2$CH$_2$CO— | 2-F | Base | 82–3 (ethyl acetate) |
| 7987 | CH$_3$ | H | H | H | 4-CH$_3$CH$_2$CH$_2$CO— | H | Base | 118–20 (ethyl acetate) |
| 7748 | H | H | H | H | 4-CH$_2$CONH$_2$ | H | Base | 167–8 (ethanol) |

TABLE I-continued

Structure:
$$R_2\text{-indole(}R_1\text{)-CH}_2\text{-C(}X_1\text{)(}X_2\text{)-NH-CH}_2\text{-CH(OH)-CH}_2\text{O-phenyl(}R_3\text{,}R_4\text{)}$$

| code No. | $X_1$ | $X_2$ | $R_1$ | $R_2$ | $R_3$ | $R_4$ | Salt or base | Melting point (°C.) (solvent of cristallisation) |
|---|---|---|---|---|---|---|---|---|
| 7747 | H | H | H | H | 4-CH$_2$COOCH$_3$ | H | Base | 98–102 (ethyl acetate-isopropyl ether) |
| 7715 | CH$_3$ | H | H | H | 4-CH$_2$CONH$_2$ | H | Base | 122–4 (ethyl acetate-isopropyl ether) |
| 7807 | CH$_3$ | H | H | H | 4-CH$_2$COOCH$_3$ | H | Base | 79–83 (ether) |
| 7798 | " | " | H | H | 4-NH—CO(CH$_2$)$_2$CH$_3$ | 2-COCH$_3$ | Base | 122 (ethyl acetate-isopropyl ether) |
| 7847 | " | " | H | H | 4-SO$_2$CH$_3$ | H | Base | 119–122 (hexane-methanol-isopropyl ether) |
| 7859 | " | " | 5'-Cl | H | 4-CH$_2$CONH$_2$ | H | Base | 155 (ethyl acetate) |
| 7860 | " | " | 5'-Cl | H | 4-CH$_2$COOCH$_3$ | H | Base | 115 (dichloromethane-isopropyl ether) |
| 7863 | " | " | H | H | 4-CH$_2$C≡N | H | Fumarate (acid) | 130 (acetone) |
| 7896 | H | H | H | H | 4-(CH$_2$)$_2$NHCOOC$_2$H$_5$ | H | Base | 101–2 (dichloromethane-isopropyl ether) |
| 7895 | H | H | H | H | 4-O—(CH$_2$)$_2$NHCOOC$_2$H$_5$ | H | Base | 111–2 (dichloromethane-isopropyl ether) |
| 40185 | C$_2$H$_5$ | H | H | H | 2-CH$_3$ | H | Fumarate (neutral) | 168–171 (ethanol) |
| 40269 | CH$_3$ | H | H | H | 4-(CH$_2$)$_2$NHCOOC$_2$H$_5$ | H | Base | Oil |
| 40405 | " | " | H | H | 4-O(CH$_2$)$_2$NHCOOC$_2$H$_5$ | H | Base | Oil |
| 40038 | " | " | 5-F | H | H | H | Base | 73–4 (hexane-dichloromethane) |

TABLE II

Structure:
$$\text{indole-CH}_2\text{-C(}X_1\text{)(}X_2\text{)-NH-CH}_2\text{CH(OH)-CH}_2\text{O-A}$$

| code no. | $X_1$ | $X_2$ | A | Salt or base | Melting point (°C.) (solvent of cristallisation) |
|---|---|---|---|---|---|
| 7701 | CH$_3$ | H | 5,6,7,8-tetrahydronaphth-1-yl | Hydrochloride | 168–9 (methanol-isopropyl) |
| 7862 | " | " | naphth-1-yl | Fumarate (neutral) | 128–130 (acetone-methanol-ether) |
| 7852 | CH$_3$ | CH$_3$ | 8-oxo-5,6,7,8-tetrahydronaphth-1-yl | Base | 76–8 (dichloromethane isopropyl) |

TABLE II-continued

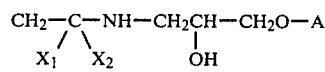

| code no. | X₁ | X₂ | A | Salt or base | Melting point (°C.) (solvent of cristallisation) |
|---|---|---|---|---|---|
| 7853 | " | " | 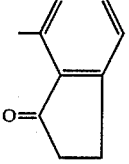 | Fumarate (acid) | 168–171 (methanol) |
| 7992 | " | " | 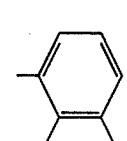 | Fumarate (acid) | 165–6 (acetone-methanol) |
| 7874 | $CH_3$ | H | 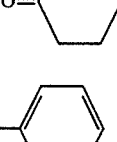 | Fumarate (acid)<br>Fumarate (neutral) | 170 (methanol)<br>187 (ethanol) |
| 40441 | $CH_3$ | $CH_3$ | 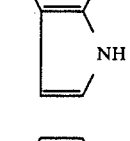 | Fumarate (neutral) | 177 (ethanol) |

TABLE III

| No CM | ID₅₀ ISORENALINE mg/kg | | | ID₅₀ NORAD-RENALINE mg/kg | EC₅₀ of DISPLACE-MENT of ³H DIHY-DROALPRENOLOL in nM | | EC₅₀ of DISPLACE-MENT of ³H CLONIDINE in nM | EC₅₀ of DISPLACE-MENT of ³H WB 4101 in nM |
|---|---|---|---|---|---|---|---|---|
| | $\beta_1$- | $\beta_2$- | $\beta_1$-$\beta_2$- | α- | Heart ($\beta_1$) | Lung ($\beta_2$) | | |
| 7743 | 1–3 | ≧3 | $\beta_1 \geq \beta_2$ | 3 | 5.300 | 6.300 | 26.500 | 2.200 |
| 7744 | 0.1 | ≧0.3 | $\beta_1 > \beta_2$ | 0.1–1 | 31 | 52 | 20.500 | 500 |
| 7748 | 1–3 | >3 | $\beta_1 > \beta_2$ | 1 | 15.000 | 57.000 | 29.500 | 2.700 |
| 7782 | 0.1–0.3 | ≧3 | $\beta_1 > \beta_2$ | 0.3 | 53 | 61.5 | 30.000 | 1.460 |
| 7798 | 1 | ≧3 | $\beta_1 > \beta_2$ | >3 | 550 | 3.700 | | |
| 7806 | 0.3 | ≧0.1 | $\beta_1 \leq \beta_2$ | 0.3 | 27.5 | 12 | 12.000 | 310 |
| 7808 | 0.3 | 1 | $\beta_1 > \beta_2$ | 0.3 | 28.5 | 24 | 25.000 | 320 |
| 7824 | 0.3 | ≧0.3 | $\beta_1 \geq \beta_2$ | 1 | 13.5 | 10 | 9.500 | 110 |
| 7859 | 0.3–1 | ≧3 | $\beta_1 > \beta_2$ | 0.3–3 | 625 | 1000 | 19.000 | 2.300 |
| 7874 | 0.01 | 0.01–0.03 | $\beta_1 \geq \beta_2$ | >0.03 | 4 | 8.2 | 20.000 | 215 |
| 7898 (isomer SS) | 0.1–0.3 | 0.3–1 | $\beta_1 > \beta_2$ | >3 | 51 | 64 | | |
| 7899 (isomer SR) | 0.3 | 0.3–1 | $\beta_1 \geq \beta_2$ | >3 | 135 | 82 | | |
| 7902 (isomer RR) | >>3 | >3 | $\beta_1 < \beta_2$ | >3 | 7400 | 3800 | | |
| 7903 (isomer RS) | 3 | 1 | $\beta_1 < \beta_2$ | 3 | 2050 | 2000 | 29.500 | 1.900 |
| 7904 | ≦0.1 | 0.1 | $\beta_1 \geq \beta_2$ | >0.3 | 7.9 | 14 | | |
| 7906 (racemic) | 0.3–1 | 1 | $\beta_1 \geq \beta_2$ | >3 | 215 | 155 | 41.000 | 1.100 |
| 7983 | 0.3 | >0.3 | $\beta_1 > \beta_2$ | >0.3 | 19 | 47 | >100.000 | 600 |
| 40038 | 0.1 | >0.3 | $\beta_1 > \beta_2$ | 0.1 | 34 | 29 | | |
| Propranolol | 0.3–1 | 0.3 | $\beta_1 = \beta_2$ | | 17.5 | 28.6 | >100.000 | 10.500 |

TABLE III-continued

| No CM | ID$_{50}$ ISORENALINE mg/kg | | | ID$_{50}$ NORAD- RENALINE mg/kg | EC$_{50}$ of DISPLACE- MENT of $^3$H DIHY- DROALPRENOLOL in nM | | EC$_{50}$ of DISPLACE- MENT of $^3$H CLONIDINE in nM | EC$_{50}$ of DISPLACE- MENT of $^3$H WB 4101 in nM |
|---|---|---|---|---|---|---|---|---|
| | $\beta_1$- | $\beta_2$- | $\beta_1$-$\beta_2$- | $\alpha$- | Heart ($\beta_1$) | Lung ($\beta_2$) | | |
| 7854 | 0.01–0.1 | 0.02–0.1 | $\beta_1 \geqq \beta_2$ | 0.1 or level | 16 | 3.7 | 6.000 | 320 |

What is claimed is:

1. A 4-[3-(1,1-dimethyl-2-(3-indolyl) ethylamino)-2-hydroxypropoxy] indole of formula

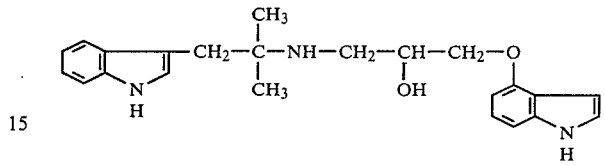

or a pharmaceutically acceptable acid addition salt thereof.

2. The 4-[3-(1,1-dimethyl-2-(3-indolyl) ethylamino)-2 hydroxypropoxy] indole fumarate of claim 1.

* * * * *